US00PP21443P2

(12) United States Plant Patent
Courtney

(10) Patent No.: US PP21,443 P2
(45) Date of Patent: Nov. 2, 2010

(54) ***SCAEVOLA* PLANT NAMED 'KINGSCABLIN'**

(50) Latin Name: *Scaevola aemula*
Varietal Denomination: Kingscablin

(75) Inventor: Patrick Courtney, Perth (AU)

(73) Assignee: Botanic Gardens and Parks Authority, West Perth (AU)

( * ) Notice: Subject to any disclaimer, the term of this patent is extended or adjusted under 35 U.S.C. 154(b) by 0 days.

(21) Appl. No.: 12/583,997

(22) Filed: Aug. 28, 2009

(51) Int. Cl.
*A01H 5/00* (2006.01)

(52) U.S. Cl. ..... Plt./363

(58) Field of Classification Search ..... Plt./363
See application file for complete search history.

*Primary Examiner*—June Hwu
(74) *Attorney, Agent, or Firm*—Audrey Charles

(57) ABSTRACT

A new and distinct cultivar of *Scaevola* plant named 'Kingscablin', characterized by its light lavender-colored flowers-with a light yellow eye, medium green-colored foliage, and vigorous, upright-mounded growth habit, is disclosed.

1 Drawing Sheet

Latin name of genus and species of plant claimed *Scaevola aemula.*

Variety denomination 'Kingscablin'.

BACKGROUND OF THE INVENTION

The present invention relates to a new and distinct cultivar of *Scaevola* plant botanically known as *Scaevola aemula* and hereinafter referred to by the cultivar name 'Kingscablin'.

The new cultivar originated in a controlled breeding program in West Perth, Australia during March 2006. The objective of the breeding program was the development of *Scaevola* cultivars that are freely flowering with unique flower coloration and a freely branching, upright-mounded growth habit.

The new *Scaevola* cultivar is the result of cross-pollination. The female (seed) parent of the new cultivar is the proprietary *Scaevola aemula* breeding selection designated 04/128d, not patented, characterized by its purple-colored flowers having a yellow eye, medium green-colored foliage, and moderately vigorous, upright growth habit. The male (pollen) parent of the new cultivar is WHIRLWIND White 'Scawihatis' U.S. Plant Pat. No. 15,003, characterized by its white-colored flowers having a greenish-yellow eye, light green-colored foliage, and vigorous, spreading and cascading growth habit. The new cultivar was discovered and selected as a single flowering plant within the progeny of the above stated cross-pollination during September 2006 in a controlled environment at West Perth, Australia.

Asexual reproduction of the new cultivar by terminal stem cuttings since September 2006 at West Perth, Australia and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Kingscablin' as a new and distinct cultivar of *Scaevola* plant:

1. Light lavender-colored flowers with a light yellow eye;
2. Medium green-colored foliage; and
3. Vigorous, upright-mounded growth habit.

Plants of the new cultivar differ from plants of the female parent primarily in flower color. Plants of the new cultivar differ from plants of the male parent primarily in flower color, foliage color, and growth habit.

Of the many commercially available *Scaevola* cultivars, the most similar in comparison to the new cultivar is SURDIVA Blue 'Bonscablue', U.S. Plant Pat. No. 19,515. However, in side by side comparisons, plants of the new cultivar differ from plants of 'Bonscablue' in at least the following characteristics:

1. Plants of the new cultivar have a more upright habit, as measured by plant height and plant width, than plants of 'Bonscablue'. In a comparison trial, plants of 'Bonscablue' had an average plant height of 8.3 cm compared with an average plant height of 13 cm for plants of 'Kingscablin'. In the same comparison trial, plants of 'Bonscablue' had an average plant width of 33.8 cm compared with an average plant width of 26.6 cm for plants of 'Kingscablin'.
2. Plants of the new cultivar have lighter colored flower petals than plants of 'Bonscablue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Kingscablin'. The plants were grown in 4.5 inch pots for 8 weeks in a greenhouse at West Chicago, Ill.

DETAILED BOTANICAL DESCRIPTION

Figure 1:
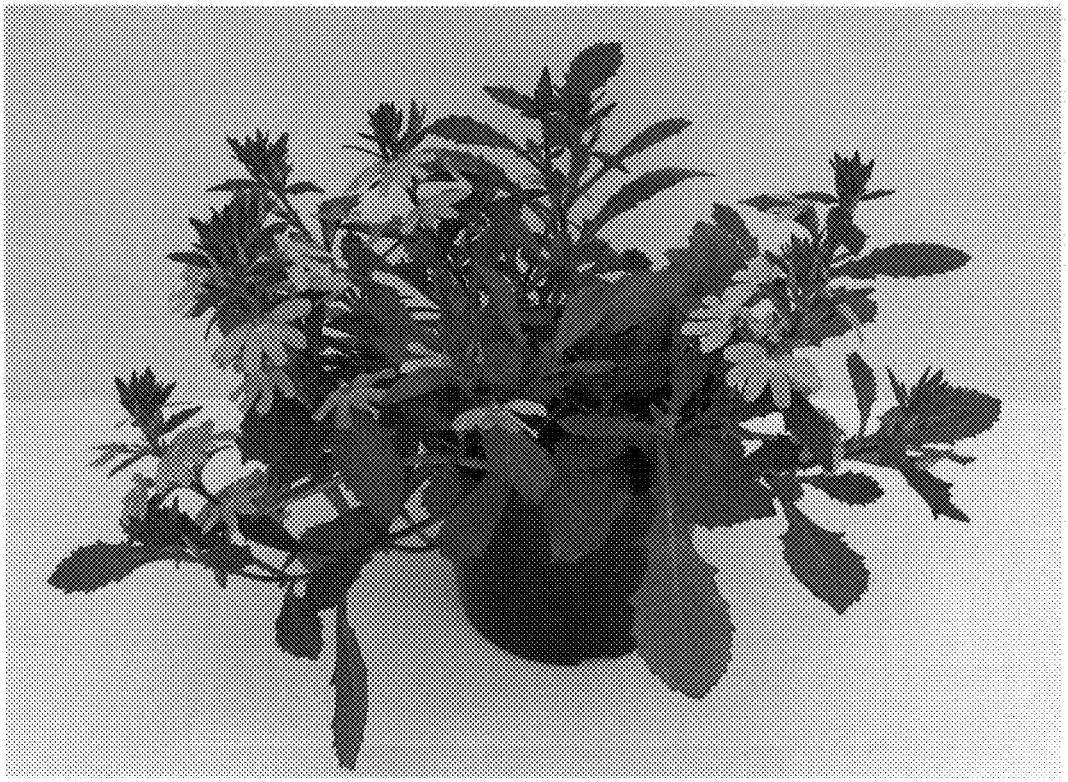
FIG. 1 illustrates a side view of the overall growth and flowering habit of 'Kingscablin'.
Figure 2:
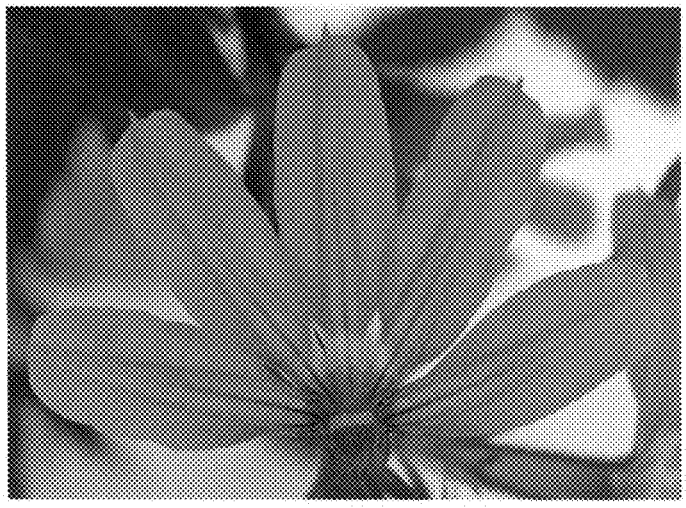
FIG. 2 illustrates a close-up view of an individual flower of 'Kingscablin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in June 2009 under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Scaevola aemula* cultivar Kingscablin.

Parentage:

*Female parent.*—Proprietary *Scaevola aemula* breeding selection designated 04/128d, not patented.

*Male parent.*—WHIRLWIND White 'Scawihatis' U.S. Plant Pat. No. 15,003.

Propagation:

*Type cutting.*—Terminal stem.

*Time to initiate roots.*—Approximately 10 to 14 days.

*Time to produce a rooted cutting.*—Approximately 24 to 28 days.

*Root description.*—Fibrous.

*Rooting habit.*—Freely branching.

Plant Description:

*Commercial crop time.*—Approximately 5 to 7 weeks from a rooted cutting to finish in a 10 cm pot.

*Growth habit and general appearance.*—Vigorous, upright-mounded growth habit.

*Size.*—Height from soil level to top of plant plane: Approximately 13.0 cm. Width: Approximately 26.6 cm.

*Branching habit.*—Freely branching. Quantity of main branches per plant: Approximately 8.

*Branch.*—Strength: Strong. Length: Approximately 15.8 cm. Diameter: Approximately 3.0 mm. Length of central internode: Approximately 2.3 cm. Texture: Pubescent. Color of young stem: 144A to 144B. Color of mature stem: 144A to 144B with an overlay of 187B.

Foliage Description:

*General description.*—Quantity of leaves per main branch: Approximately 6. Fragrance: None. Form: Simple. Arrangement on flowering stem: Alternate.

*Leaves.*—Aspect: At acute angle to stem with tip turning downward. Shape: Spatulate. Margin: Serrate. Apex: Acute. Base: Attenuate. Venation pattern: Pinnate, arcuate. Length of mature leaf: Approximately 6.5 cm. Width of mature leaf: Approximately 2.7 cm. Texture of upper and lower surfaces: Pubescent. Color of upper surface of young foliage: 137A with venation of 144B. Color of lower surface of young foliage: 138B with venation of 144D to indistinguishable. Color of upper surface of mature foliage: 137B often with 187A on margins with venation of 144B. Color of lower surface of mature foliage: 138B with venation of 144B to indistinguishable.

*Petiole.*—Length: Approximately 2.7 cm. Diameter: Approximately 3.0 mm. Texture: Pubescent. Color: 144B with a faint overlay 187B on the upper surface.

Flowering Description:

*Flowering habit.*—'Kingscablin' is freely flowering under outdoor growing conditions with substantially continuous blooming from spring through autumn and year-round in greenhouse environment.

*Lastingness of individual flower on the plant.*—Approximately 7 days.

Flower Description:

*General description.*—Type: Zygomorphic, semi-circular, fan shaped flowers with five petals fused at the base forming a tubular flower throat. Flower throat adaxially slit to base. Arrangement: Solitary, sessile. Flowers face upward and outward. Quantity per plant: Approximately 46. Fragrance: None.

*Bud.*—Rate of opening: Generally takes 1 to 2 days for bud to progress from first color to fully open flower. Quantity per plant: Approximately 10 terminal clusters.

*Bud just before opening.*—Shape: Lanceolate. Length: Approximately 1.6 cm. Diameter: Approximately 2.0 mm. Texture: Pubescent. Color: 144B with base of 144A.

*Corolla.*—Length (including tube): Approximately 2.4 cm. Width: Approximately 2.6 cm.

*Petals.*—Quantity: 5, fused at base to form a tube. Shape: Oblong. Margin: Entire. Apex: Cuspidate. Length from tube: Approximately 1.2 cm. Width: Approximately 5.0 mm. Texture of upper surface: Glabrous. Texture of lower surface: Pubescent on central band. Color of upper surface when first and fully open: N88C to N88D with irregular areas of 2B at the base of the central three petals. Color of lower surface when first and fully open: N88C to N88D with a central longitudinal band of 145D.

*Corolla tube.*—Length: Approximately 1.4 cm. Diameter at distal end: Approximately 3.0 mm. Diameter at proximal end: Approximately 1.0 mm. Texture of inner and outer surfaces: Densely pubescent. Color of inner surface: 154B with venation of N77A and N144D at throat opening. Color of outer surface: 145C with venation of N77A.

*Sepals.*—Quantity per flower: One larger and somewhat fleshy sepal and two smaller sepals fused at the base of the flower. Shape: Larger sepal elliptic; smaller sepals acicular. Apex of all sepals: Acute. Margin of larger sepal: Tridentate. Margin of smaller sepals: Entire. Length of larger sepal: Approximately 3.0 cm. Length of smaller sepals: Approximately 7.0 mm. Width of larger sepal: Approximately 1.5 cm. Width of smaller sepals: Approximately 1.0 mm. Texture of upper and lower surfaces of all sepals: Sparsely pubescent. Color of upper surface of all sepals: 137A. Color of lower surface of all sepals: 138B.

*Reproductive organs.*—Androecium: Stamen quantity: 5. Stamen length: Approximately 9.0 mm. Filament length: Approximately 7.0 mm. Filament color: 155D. Anther shape: Oblong. Anther length: Approximately 2.0 mm. Anther color: 4C. Pollen amount: Moderate. Pollen color: 4D. Gynoecium: Pistil quantity: 1 per flower. Pistil length: Approximately 1.4 cm. Stigma shape: Bilobed, slightly recurved and enclosed in a hairy cup. Stigma diameter: Approximately 3.0 mm. Stigma color: 1D. Style length: Approximately 1.1 cm. Style color: 145C with streaks of N77A. Hairs of pure white cupped around stigma with hairs of N77A tipped in pure white at base of cup. Ovary length: Approximately 2.0 mm. Ovary color: 145A.

Seed and fruit production: Neither seed nor fruit production has been observed.

Disease and pest resistance: Resistance to pathogens and pests common to *Scaevola* has not been observed.

What is claimed is:

1. A new and distinct cultivar of *Scaevola* plant named 'Kingscablin', substantially as herein shown and described.

* * * * *